United States Patent [19]

Mimura et al.

[11] Patent Number: 5,719,059
[45] Date of Patent: Feb. 17, 1998

[54] REAGENT MANAGEMENT METHOD AND APPARATUS THEREFOR

[75] Inventors: Tomonori Mimura, Tomobe-machi; Atsushi Takahashi, Hitachinaka, both of Japan

[73] Assignee: Hitachi, Ltd., Tokyo, Japan

[21] Appl. No.: 674,525

[22] Filed: Jul. 2, 1996

[30] Foreign Application Priority Data

Jul. 11, 1995 [JP] Japan ................... 7-174616

[51] Int. Cl.$^6$ ................................................ G01N 37/00
[52] U.S. Cl. ................................. 436/50; 436/43; 436/47; 422/64; 422/67
[58] Field of Search ........................... 422/63, 64, 67, 422/100; 436/43, 47, 48, 49, 50, 174, 180

[56] References Cited

U.S. PATENT DOCUMENTS

| | | | |
|---|---|---|---|
| 4,346,056 | 8/1982 | Sakurada | 422/64 |
| 4,451,433 | 5/1984 | Yamashita et al. | 422/63 |
| 4,455,280 | 6/1984 | Shinohara et al. | 422/63 |
| 5,051,238 | 9/1991 | Umetsu et al. | 422/64 |
| 5,100,622 | 3/1992 | Mimura et al. | 422/67 |
| 5,424,036 | 6/1995 | Ushikubo | 422/64 |

FOREIGN PATENT DOCUMENTS

| | | |
|---|---|---|
| 60-17362 | 1/1985 | Japan . |
| 5-281242 | 10/1993 | Japan . |

*Primary Examiner*—Long V. Le
*Attorney, Agent, or Firm*—Fay, Sharpe, Beall, Fagan, Minnich & McKee

[57] ABSTRACT

An autoanalyzer prevents data abnormalities by managing the analyzable number of times corresponding to each reagent bottle as a result of reagent deterioration caused by reagent replenishment, or the like, to thereby make it possible to perform higher-accuracy analysis management. Before an analyzing operation is executed by an analyzer, the term of validation of each reagent bottle set in the analyzer is checked. If the term expires, the use of a reagent in the reagent bottle is stopped. Further, the identification code of each used reagent bottle is stored in a memory so that the use of a reagent in the used reagent bottle is prohibited when the used reagent bottle is set on a reagent disk again.

8 Claims, 4 Drawing Sheets

REAGENT MANAGEMENT METHOD AND APPARATUS THEREFOR

BACKGROUND OF THE INVENTION

The present invention relates to a reagent management method and apparatus in use for analyzing analytical items in an automatic chemical analyzer, an automatic immuno assay analyzer, or the like, and particularly relates to a reagent management method and apparatus in the case where a plurality of reagent solutions are used.

In the case of analysis of a living sample, it is general that the optical characteristic of a reaction solution obtained by mixing the sample and a reagent corresponding to the analytical item for analyzing the sample is measured to thereby calculate the concentration of the analytical item. The method of supplying a reagent solution to a reaction cell on a reaction line correspondingly to the analytical item is classified into a pipetter method using a reagent suction and exhaust nozzle and a dispenser method using a reagent flow tube. In each method, it is necessary to monitor the remaining quantity of the reagent solution in the reagent solution bottle.

As such an example, JP-A-60-17362 is known. This document discloses a reagent management method in the case where each reagent solution is distributively injected into a reaction cell by using a reagent distributive injection probe having a liquid level detecting function. That is, the remaining quantity of each reagent solution is obtained on the basis of the output of a liquid level detector, and data indicating the kind of the reagent and the date of production are expressed in a bar code or a binary code on the surface of the reagent solution bottle in advance so that the data are read by a data reader to check the kind of the reagent solution to thereby manage the remaining quantity of the reagent without any operation of inputting the kind of the reagent.

Another disclosure concerning reagent management is in JP-A-5-281242. According to document, the remaining quantity of the reagent solution is managed by detecting of the level thereof, and a judgment portion judges that the reagent bottle has been refilled or replenished when the remaining quantity of the reagent solution in the reagent solution bottle is more than that detected previously.

According to the apparatus and methods disclosed in JP-A-60-17362 and JP-A-5-281242, the respective remaining quantities of reagents in the reagent solution bottle for a plurality of analytical items can be determined. Moreover, even in the case where the remaining analyzable number of times of a reagent solution in an initial-state reagent solution bottle becomes zero, the analyzing operation for a corresponding analytical item can be continued by replenishing the reagent solution bottle with the same kind of reagent solution.

When the reagent solution bottle is replenished with a deteriorated reagent solution, it is however impossible to maintain the measurement result for each analytical item in high analyzing accuracy. Because a reagent for clinical analysis may contain an enzyme, antiserum, or the like, the deterioration of the reagent progresses gradually after the reagent solution bottle is once opened. Particularly when a long time is passed after the reagent solution bottle is opened, not only is the reagent condensed by evaporation, but also the reagent solution is contaminated with bacteria or fungi. If the reagent solution bottle in use is replenished with such a reagent solution in which a long time is passed after opening, the composition of the reagent solution is changed. If the analyzing operation is continued by using a degraded reagent solution or by using a reagent solution mixed with a degraded reagent solution, accurate analysis results with respect to respective analytical items cannot be obtained because abnormalities occurs frequently in the measurement data.

SUMMARY OF THE INVENTION

An object of the present invention is to provide a reagent management method and apparatus in which a degraded reagent is prevented from being used in measurement for a corresponding analytical item so that a reliable result of analysis can be obtained.

The present invention, in the case of distributively injecting a reagent corresponding to an analytical item into a reaction cell of an analyzer, registers information for identification of used reagent solution bottles in a storage portion in advance, judges by a judgment means whether a reagent solution bottle set in a reagent setting portion has been registered or not, and outputs an alarm when the judgment proves that the reagent solution bottle is registered as a used one.

An analyzer to which the present invention is applied comprises: a reaction line having a large number of reaction cells; a sample distributer for supplying samples (or analytes) to the reaction cells; a reagent distributer for supplying reagent solutions corresponding to analytical items to the reaction cells; a measurement portion for measuring reaction solutions formed in the reaction cells; and a control arithmetic operation portion for controlling the operations of respective constituent parts and performing arithmetic operations of measurement data to output measurement results to an output device. The reagent distributer has a distributive injector for distributively injecting a reagent solution of a reagent solution bottle selected from a large number of reagent solution bottles into a corresponding reaction cell. As the distributive injector, it is possible to use a pipetter having a reagent suction and exhaust nozzle for sucking a reagent solution from each reagent solution bottle and for injecting the reagent solution into a reaction cell, or a dispenser for leading reagents to reaction cells for corresponding analytical items through reagent feed tubes arranged in respective reagent solution bottles.

Various kinds of information in the form of a bar code, a binary code or a character string is indicated on the respective outer walls of reagent solution bottles prepared for various analytical items. For example, the information contains the kind of the reagent indicating the classification of analytical items, the sequence of distributively injected reagents discriminating between first, second and third reagents, the quantity of the reagent allowed to be used in each reagent solution bottle, the quantity of the distributively injected reagent indicating the dosage of the reagent, the maximum analyzable number of times with respect to each reagent solution bottle, the size of each reagent solution bottle, the term (date) of validation of the reagent, the sequence number peculiar to the reagent solution bottle, the data of production of the reagent, the production lot number of the reagent, and so on. Of these kinds of information, information except the kind of the reagent and the sequence of distributively injected reagents can be provided in the form of a floppy disk or in the form of a visual confirmation sheet so that the floppy disk or visual confirmation sheet is delivered when each reagent solution bottle is delivered.

The information indicated on the outer wall of each reagent solution bottle is read by a reader such as a bar-code reader and stored in a storage portion of the analyzer so as to be related to the sequence number as reagent solution bottle identification information. Information in the form of a floppy disk is stored in a storage portion of the analyzer from a floppy disk information reader so as to be related to the sequence number of the reagent solution bottle when the reagent solution bottle is set in the analyzer. On the other hand, information in the form of a visual confirmation sheet is inputted through an input device by an operator and stored in a storage portion of the analyzer so as to be related to the sequence number of the reagent solution bottle.

The "used reagent solution bottle" used in the present invention means not only a solution bottle which is recognized to be a bottle used once but also a solution bottle regarded as improper for the continuous use of the reagent solution, for example, a solution bottle recognized as replenished with another solution because of the increase of the quantity of solution in the middle of the distributively injecting operation repeated. As the method of outputting an alarm, it is possible to use a method in which the operation of distributively injecting the reagent solution is stopped and an alarm is issued by voice or display when the reagent solution bottle is improper, a method in which, even in the case where the reagent solution bottle is improper, the analyzing operation is continued by using the reagent solution in the improper reagent solution bottle and giving a warning indication in the form of a symbol, a character, or the like to the analysis result data thus obtained, and so on.

In a preferred embodiment of the present invention, with respect to each reagent solution bottle (reagent bottle), information, such as the sequence of reagents to be distributively injected, the size of the reagent solution bottle, the maximum analyzable number of times, etc., is read from the indication on the outer wall of each reagent solution bottle, from a floppy disk or inputted through a keyboard, and the information is stored in a storage portion of the analyzer. Information such as the sequence number peculiar to each reagent solution bottle, the term of validation of each reagent, the production lot number, etc., is read by a reader on the basis of the information indicated on the outer wall of the reagent solution bottle and stored so as to be related to the reagent setting position recognized on the basis of information outputted from a reagent bottle housing portion having a reagent table and related to the analytical item designated on the basis of the inputting operation through an input device. On this occasion, the maximum analyzable number of times stored by reagent solution bottle is set as an initial value of the number of times by which the reagent in the reagent solution bottle is allowed to be tested.

On the basis of the read information concerning the term of validation of the reagent, a judgment is made as to whether the term expires or not. If the term in a reagent solution bottle expires, an alarm is displayed on a display device such as a CRT to stop the use of the reagent solution bottle and, at the same time, a warning is outputted for indicating the necessity of exchanging the reagent solution bottle to a new one, and the program is locked so that the operation of distributively injecting the reagent from the reagent solution bottle is not carried out by the reagent distributive injector. If the term does not expire, the execution of the distributively injecting operation is not prevented.

Whenever the reagent solution is distributively injected into the reaction cell after the start of the analyzing operation, the number of times by which the reagent is allowed to be tested (that is, the remaining number of times of; and is decreased by one. At the point of time when the remaining number of times of test reaches zero, the distributive injection of the reagent from the reagent solution bottle is stopped and a warning is outputted for indicating the necessity of replacing the reagent solution bottle by a new one. At this time, the sequence number as information for identification of the reagent solution bottle is registered into the used-reagent-solution-bottle memory area.

In the period of the execution of the analyzing operation, the remaining number of times of test calculated on the basis of the result of reagent solution level detection, or the like, with respect to each reagent solution bottle is compared with the remaining number of times of test stored in the previous cycle of distributive injection. If the remaining number of times of test in the current cycle is larger than that in the previous cycle, the reagent solution bottle is judged as replenished with a reagent solution from another solution bottle and a warning is outputted for indicating the fact that the reagent solution bottle is improper for use. On this occasion, the distributive injection from the reagent solution bottle is stopped or the distributive injection is continued and warning information is given to the analysis result. Also in the case where the remaining number of times of test in a reagent solution bottle is increased in the process of the analyzing operation, the sequence number of the solution bottle is registered into the used-reagent-solution bottle memory area.

Thereafter, with the setting of reagent solution bottles for analytical items in the reagent bottle housing portion, the sequence number of each reagent solution bottle is read and a judgment is made as to whether the sequence number has been registered in the used-reagent-solution-bottle memory area or not. If the identification number peculiar to the solution bottle has been already registered, a warning is issued for indicating the fact that the reagent solution bottle is improper and, at the same time, the distributive injection of the reagent is stopped or warning information given to display data of the analysis result with respect to the analytic item using the reagent is displayed after the distributive injection of the reagent is continued.

DESCRIPTION OF THE PREFERRED EMBODIMENTS

Figure 1:
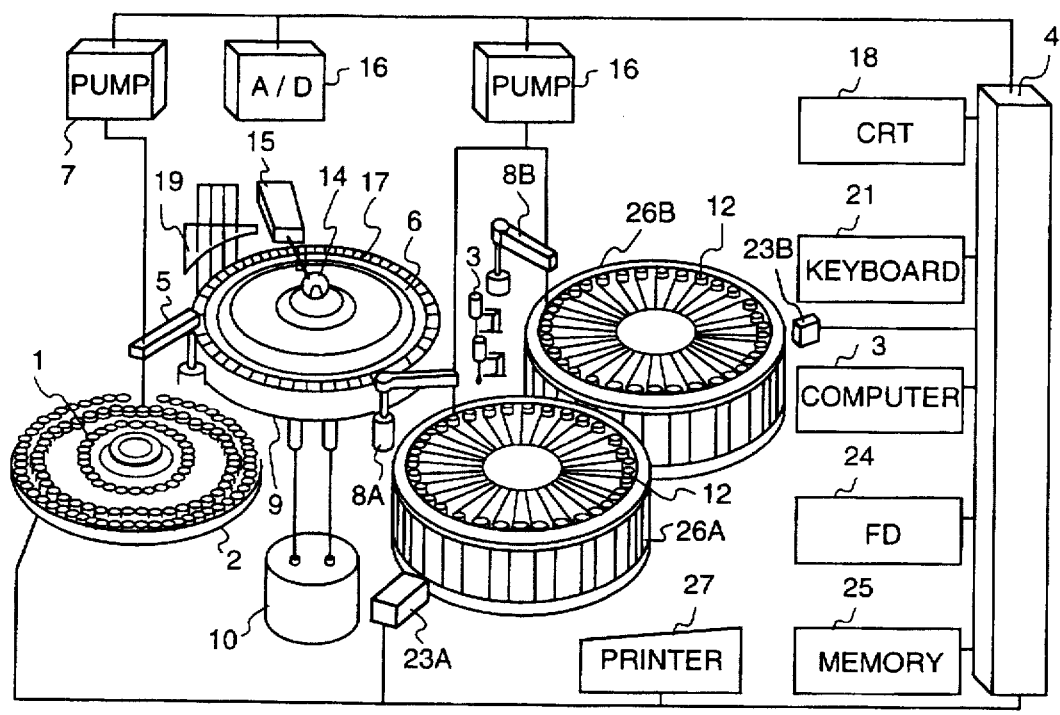
FIG. 1 is a schematic view showing the overall configuration of an autoanalyzer as an embodiment of the present invention.
Figure 3:
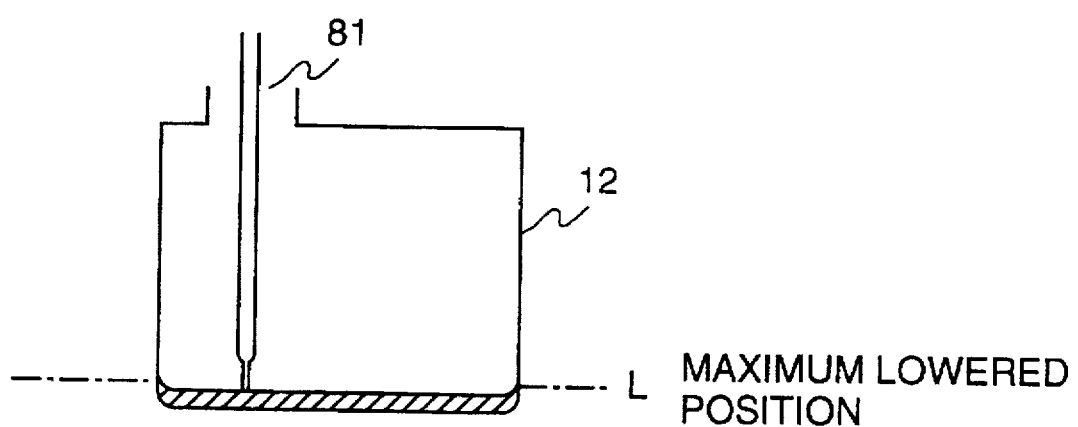
FIG. 3 is a view for explaining the positional relation between the maximum lowered position of a reagent suction and exhaust nozzle and the height of a reagent bottle in the analyzer depicted in FIG. 1.
Figure 4:
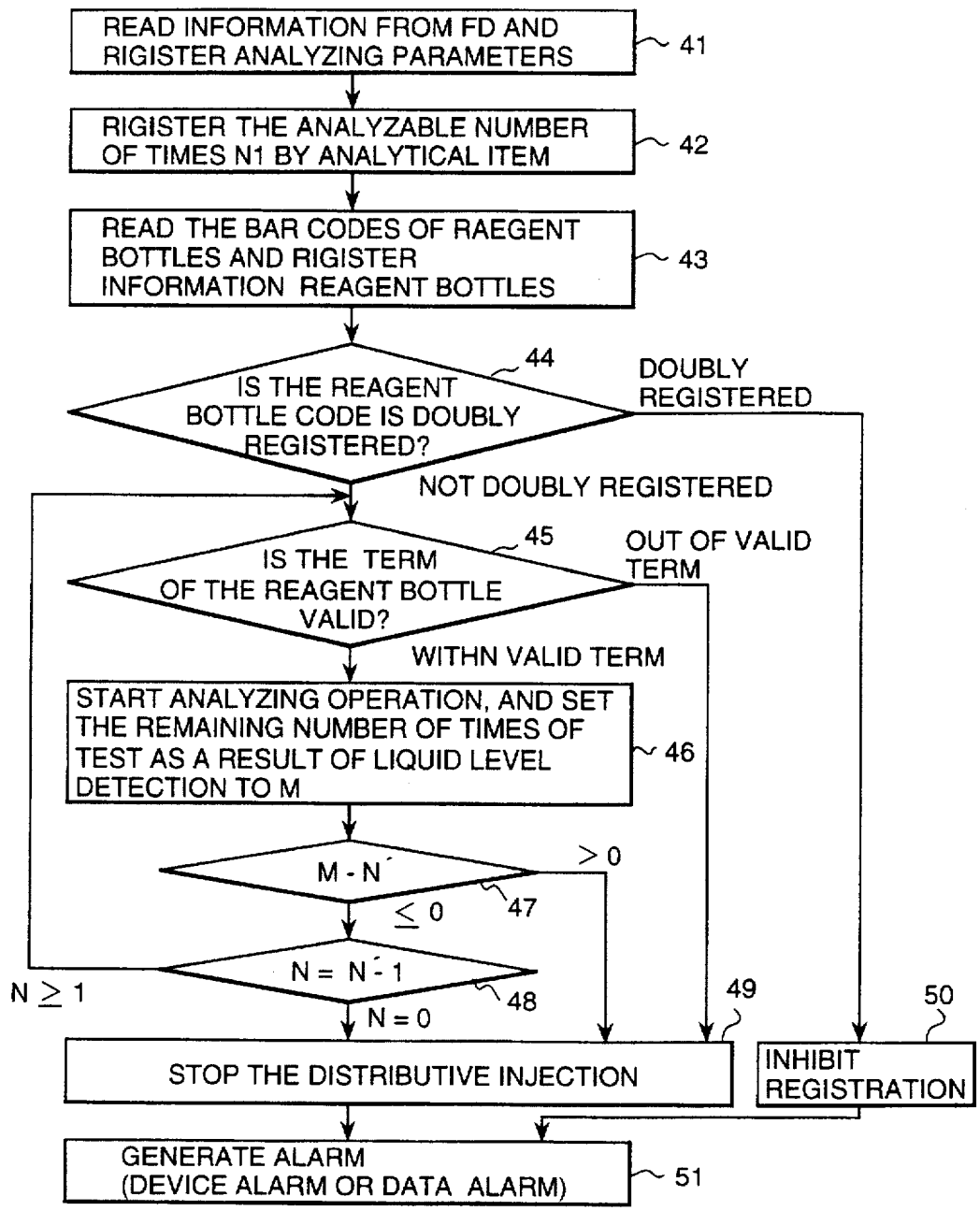
FIG. 4 is a flow chart for explaining a checking state for reagent management in the analyzer depicted in FIG. 1.
Figure 5:
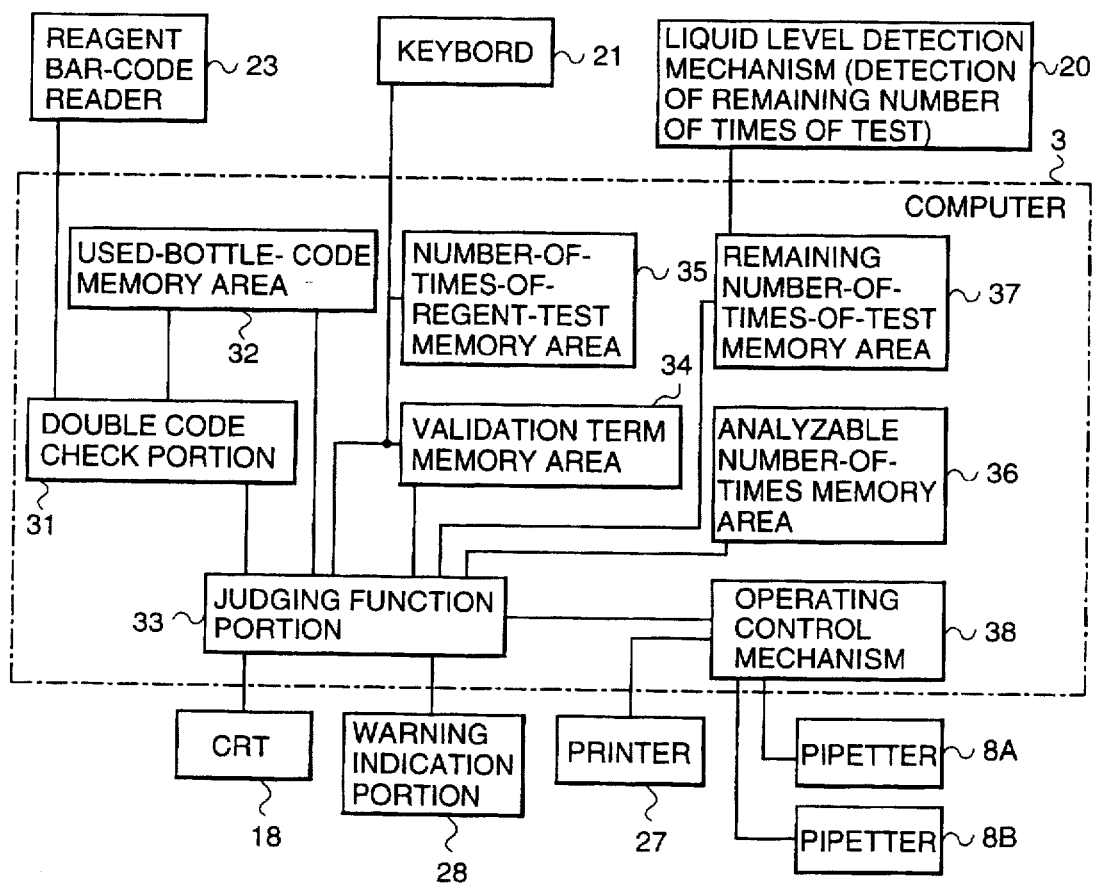
FIG. 5 is a functional explanatory view of a computer concerning reagent management.

An embodiment of the present invention will be described with reference to FIGS. 1 through 5. FIG. 1 is a schematic view showing the overall configuration of a multi-item chemical analyzer for analyzing a plurality of analytical items in a living body sample by photometry, FIG. 2 is an external appearance view showing an example of a reagent bottle with reagent information indicated on its outer wall, FIG. 3 is a view for explaining the relation between the reagent bottle and the height of the maximum lowered position of a reagent suction and exhaust nozzle, FIG. 4 is a flow chart for explaining information processing following the distributive injection of a reagent, and FIG. 5 is a view for explaining the function of a computer containing a judgment means for information processing.

In FIG. 1, a large number of sample containers 1 in which samples are contained respectively are arranged on a sample carrying disk 2. A suction and exhaust nozzle of a sample distributive injection mechanism 5 is connected to a sample syringe pump 7. The respective operations of the pump 7 and sample distributive injection mechanism 5 are controlled by a computer 3 which controls the operations of respective mechanical portions and computes measurement data through an interface 4. A large number of reaction cells 6 are arranged on a reaction table 17 which is provided so as to be rotatable with respect to a reaction bath 9. The arrangement of the large number of reaction cells 6 on the reaction table 17 forms a reaction line. A constant-temperature liquid maintained at 37 degrees Celsius is supplied from a constant-temperature liquid supply portion 10 to the reaction bath 9. A multi-wavelength photometer has a light source 14 and a multi-wavelength spectroscope 15. The reaction table 17 is rotationally carried so that the arrangement of the reaction cells 6 crosses a light beam from the light source 14. Used reaction cells 6 are cleaned by a cleaning mechanism 19 and subjected to reuse. A stirring mechanism 13 mixes an analyte or sample supplied to each reaction cell 6 with a reagent solution corresponding to an analytical item for the analyte. A measurement signal obtained by the multi-wavelength spectroscope 15 on the basis of the reaction solution is converted from an analog signal to a digital signal by an A/D converter 16, so that the digital signal is supplied to the computer 3.

Various kinds of reagent bottles 12 corresponding to respective analytical items are arranged on first and second reagent disks 26A and 26B circularly. That is, the disks 26A and 26B are reagent bottle housing portions each of which can be rotated to select a reagent from reagents housed therein. A bar-code reader 23A is disposed in proximity to the disk 26A whereas a bar-code reader 23B is disposed in proximity to the disk 26B. A reagent distributive injector includes reagent distributive injection pipetters 8A and 8B, and a reagent syringe pump 11. Each of the pipetters 8A and 8B is designed so that a predetermined quantity of a reagent solution in a reagent bottle 12 stopped in the suction position is sucked/held into the suction and exhaust nozzle, and that a reagent solution held in a reaction cell 6 stopped in the reagent acceptance position is discharged by rotating the suction and exhaust nozzle on the arrangement of reaction cells. The reagent solution distributively injected on this occasion is of a kind corresponding to an analytical item assigned to each reaction cell.

Figure 2:
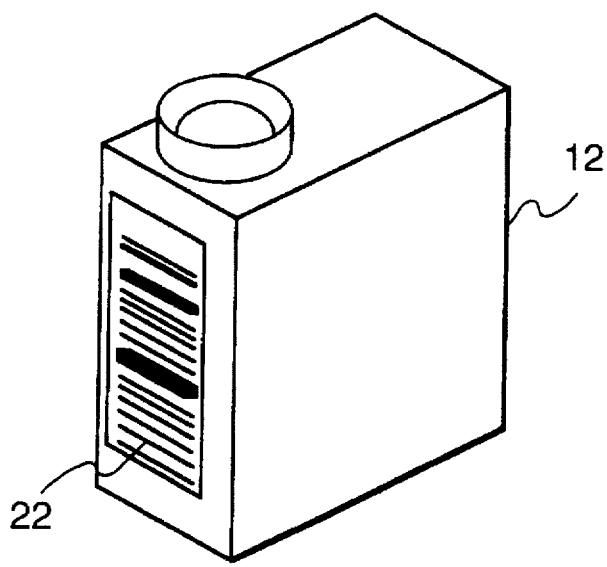
FIG. 2 is an external appearance view of a reagent bottle used in the analyzer depicted in FIG. 1.

As shown in FIG. 2, a reagent bar-code label 22 having a bar code printed is stuck on the outer wall of each reagent bottle 12. The information expressed by the bar code includes, for example, the reagent bottle code constituted by a sequence number given to each bottle peculiarly, the size of the bottle, the term of validity of a reagent solution in the bottle, the sequence of distributively injected reagents discriminating between first, second and third reagents, the maximum number of times by which the reagent solution can be analyzed, the quantity of the distributively injected reagent indicating the quantity of the reagent used in a distributive injection cycle, the production lot number, and so on. The reagent information read from the respective reagent bottles 12 by the bar-code readers 23A and 23B is stored in corresponding memory areas of a storage portion 25 or the micro-computer 3. Whenever a reagent bottle 12 is housed in the reagent disk 26A or 26B, reagent information is read from the reagent bottle 12 by the bar-code reader 23A or 23B. At the same time, a signal indicating the set position of the reagent bottle is outputted from a rotation angle detection portion provided in each reagent disk and inputted into the computer 3 through the interface 4. The reagent information, the bottle set position and the analytic item are stored so as to be related to each other.

An operator can input various kinds of information by using a screen of CRT 18 and a keyboard 21. Measurement results of analytic items can be printed by a printer 27 or displayed by the CRT 18. Information in a floppy disk 24 is read by a floppy disk reader and stored in a corresponding memory area of the storage portion 25 or the computer 3. The information stored in the floppy disk 24 may include, for example, analytical item codes each expressed in five digits, parameters used in common for analytic items, parameters stored separately with respect to reagent bottles, and so on. Of the information, parameters used in common to analytical items are wavelengths used in the photometer, the quantity of each sample, the method of calibration, the concentration of each standard solution, the number of standard solutions, the limit value for checking the abnormality of analysis, and so on. Parameters stored separately with respect to reagent bottles are the classification of each reagent, the sequence of reagents to be distributively injected, the code of each reagent bottle, the volume of each reagent solution, the quantity of each reagent to be distributively injected, the maximum number of times by which analysis can be made (the maximum analyzable number of times), the date of production of reagent, and so on.

Besides the information read from the floppy disk 24, information such as the operating conditions of respective mechanical portions in the analyzer, the analytical parameters of respective analytical items, judgment logic for management of respective reagent bottles, the maximum analyzable number of times read from each reagent bottle, the result of analysis, and so on, is stored in the storage portion 25. The information of each reagent is provided in the form of a floppy disk by the maker of the reagent when the bottle of the reagent is delivered. If such reagent information is not provided in the form of a floppy disk, information described in a visual confirmation sheet attached to the reagent bottle can be inputted into the analyzer by the operator using the display and the keyboard 21.

As shown in FIG. 3, each of the reagent distributive injection pipetters 8A and 8B is provided with a reagent suction and exhaust nozzle 81. Although this nozzle 81 can be moved vertically and rotated horizontally, the maximum lowered position L of the nozzle 81 is set so that the nozzle 81 does not touch the bottom of each reagent bottle 12. Therefore, an inevitably remaining quantity of reagent solution in addition to the effective volume of the reagent is put in the reagent bottle 12. The reagent suction and exhaust nozzle 81 has a liquid level detection electrode by which the liquid level of the reagent bottle is detected whenever the reagent solution is distributively injected. On the basis of the height of the liquid level thus detected and the sectional area of the reagent bottle, the remaining quantity of the reagent or the number of times by which the remaining reagent is allowed to be tested is calculated by the computer 3 and stored in a predetermined memory area.

As shown in FIG. 5, the computer 3 has memory areas such as a used-bottle-code memory area 32, a reagent validation term memory area 34, a number-of-times-of-reagent-test memory area 35, an analyzable-number-oftimes memory area 36, a remaining number-of-times-of-test memory area 37, etc., a double code check portion 31, a judging function portion 33, an operating control mechanism 38, and so on. A signal from a liquid level detector of a liquid level detection mechanism 20 is inputted into the computer 3, so that the number of times by which the remaining reagent is allowed to be tested as stored in the remaining number-of-times-of-test memory area 37 is changed whenever the reagent solution is distributively injected. The result judged by the judging function portion 33 can be displayed by the CRT 18, indicated by a warning indication portion 28, printed by the printer 27, etc.

The computer 3 searches all items already registered as analytical parameters to retrieve information relating to the corresponding item and reagent bottle code by using the reagent bottle code as a keyword, reads the maximum analyzable number of times with the reagent bottle on the basis of the retrieved information, and stores the maximum analyzable number of times as the number of times of reagent test of the reagent bottle into the memory area 35. The number of times of reagent test is stored separately from the maximum analyzable number of times stored by analytical item. In the period of analysis, the number of times of reagent test of the reagent bottle 12 is decreased by one whenever the distributive injection of the reagent is executed once, whereas the maximum analyzable number of times is held as it was registered as a parameter.

Analysis as the whole in the autoanalyzer is carried out in the sequence of sapling, reagent distributive injection, stirring, photometering, reaction cell cleaning, and data processing for conversion of the concentration, or the like. A plurality of sample containers 1 containing respective samples are set on the sample disk 2. The sample disk 2 is controlled by the computer 3 through the interface 4. The analyte disk 2 is rotated so that samples come under a probe of the analyte distributive injection mechanism 5 in a sequence of samples to be analyzed. When a sample bottle 1 comes under the probe, a predetermined quantity of the analyte in the given sample bottle 1 is distributively injected into a reaction cell 6 by the operation of the analyte pump 7 connected to the analyte distributive injection mechanism 5.

Upon reception of the sample, the reaction cell 6 is moved to the first reagent addition position in the reaction bath 9. To the reaction cell 6 thus moved, added is a predetermined quantity of a reagent sucked from a reagent bottle 12 by the operation of the reagent pump 11 connected to the suction and exhaust nozzle of the reagent distributive injection pipetter 8. After the addition of the first reagent, the reaction cell 6 is moved to the position of the stirring mechanism 13 and first stirring is performed.

Assuming now that reagents up to the fourth reagent are set on the reagent disks 26A and 26B, then the aforementioned cycle of reagent addition and stirring is repeated for each of the reagents (from the first reagent to the fourth reagent).

After the contents of the reaction cell 6 are stirred, the reaction cell 6 passes through a beam of light emitted from the light source. On this occasion, absorbency is detected as an absorbency signal by the multi-wavelength spectroscope 15. The absorbency signal thus detected is converted into a digital signal by the A/D converter 16. The digital signal is inputted into the computer 3 through the interface 4 and converted into the concentration of the analyte by the computer 3. After conversion into the concentration, the thus obtained data is printed out by the printer 27 through the interface 4 or displayed on the screen of the CRT 18. After the photometering, the reaction cell 6 is moved to the position of the cleaning mechanism 19. In the position of the cleaning mechanism 19, the content in the reaction cell 6 is discharged by the bottle cleaning pump and cleaned with a cleaning solution to be prepared for the next analysis.

In the case of the ordinary operation, in the period of execution of analysis, each of the reagent distributive injection pipetters 8A and 8B executes distributive injection while the liquid level is detected, and the number of times of reagent test in the reagent bottle 12 is decreased by one whenever the distributive injection is carried out once. When each of the reagent distributive injection pipetters 8A and 8B is moved down, in the reagent bottle 12, to the depth of the maximum lowered position L determined in the analyzer, the position L is regarded as the bottom of the reagent bottle 12 and the distributive injection from the reagent bottle 12 is stopped. In the case where the reagent bottle 12 contains a larger quantity of the reagent than a predetermined quantity, the number of times of reagent test is set to zero before the quantity of the reagent in the reagent bottle 12 reaches zero. In this stage, the distributive injection from the reagent bottle is stopped even if the reagent remains in the reagent bottle. At the same time, an alarm is issued and indicated on the display. All the information of the reagent bottle 12, the reagent code and the analyzable number of times with the reagent bottle are stored, and an alarm is issued without starting distributive injection even when the bottle which has been used once and in which the number of times of reagent test has reached zero is set again.

The operation of reagent management will be described with reference to FIGS. 4 and 5. In step 41, information is read from the floppy disk 24, by which various kinds of information are taken in before the analyzing operation of the analyzer starts so that the value of the maximum analyzable number of times is stored both in the number-of-times-of-reagent-test memory area 35 and in the analyzable-number-of-times memory area 36. That is, the analyzable number of times N1 is registered by analytical item (step 42).

In step 43, the bar codes of reagent bottles 12 set on the reagent disks 26A and 26B are read by the bar-code readers 23A and 23B so that information indicated on the reagent bottles 12 is registered into a predetermined memory. With the registration of information, the term of validation of each of the reagent bottles 12 is stored in the validation term memory area 34. In step 44, a judgment is made as to whether the reagent bottle code is doubly registered or not. In this case, the double code check portion 31 extracts storage information from the memory area 32 and makes the judging function portion 33 judge whether the reagent bottle code read by each of the bar-code readers 23A and 23B is coincident with the bottle code already registered in the used-bottle-code memory area 32 or not. If there is a coincident code, the reagent solution in the current reagent bottle 12 is regarded as improper so that registration cannot be made in step 50 and then an alarm is generated in the CRT 18 or in the warning indication portion 28 in step 51. If there is no coincident code, the reagent solution in the current reagent bottle 12 is concluded to be available and the situation of the routine goes to step 45.

In the step 45, before the start of the analyzing operation, that is, before the execution of reagent distributive injection, a judgment is made as to whether the term of validation of the reagent bottle 12 is proper or not. On this occasion, the term of validation of the reagent bottle obtained from the validation term memory area 34 storing information indicated on the reagent bottle is checked by the judging function portion 33 on the basis of the date obtained from a timer function contained in the computer 3. If a decision is made so that the term of validation of the reagent bottle 12 expires, the distributively injecting operation of each of the reagent distributive injection pipetters 8A and 8B is masked so as not to be executed in the position of the current reagent bottle and, at the same time, an alarm is generated in the CRT 18 or in the warning indication portion 28. If the term in the reagent bottle does not expire, there is no limitation given to the operation of the reagent distributive injection pipetter.

In step 46, the analyzing operation starts so that the reagent distributive injector executes its distributively injecting operation normally. The value stored in the number-of-times-of reagent-test memory area 35 for every reagent is decreased by one whenever the distributive injection is executed once. The latest value is made N'. The liquid level of the reagent solution in each reagent bottle 12 is measured with the reagent distributively injecting operation for every reagent solution, so that the remaining number of times of test is calculated on the basis of a signal given from the liquid level detection mechanism 20 and stored as the value M in the remaining number-of-times-of-test memory area 37.

In step 47, the value N' in the number-of-times-of-reagent-test memory area 35 is compared with the value M in the remaining number-of-times-of-test memory area 37 with respect to the same reagent, so that the judging function portion 33 judges from the comparison whether the distributively injecting operation is stopped or not. That is, in the normal case, the remaining number of times M of test based on the result of liquid level detection is not larger than the latest number of times N' obtained by decreasing on the basis of the distributive injection number of times. Hence, if the value M is larger than the value N', a decision is made that the reagent is deteriorated because of replenishment of the reagent from another reagent bottle and the distributively injecting operation of the reagent bottle is masked. If the value M is not larger than the value N', the distributively injecting operation is not masked. Alternatively, there may be employed a method in which the same judgement as described above is made by comparison between the remaining number of times of test based on the previous cycle of liquid level detection and the remaining number of times of test based on the current cycle of liquid level detection with respect to the same reagent bottle. The value stored in the remaining number-of-times-of-test memory area 37 is updated whenever the liquid level detection is made.

In step 48, the number of times N' in the number-of-times-of reagent-test memory area 35 is decreased by one. This value N' is equivalent to the difference between the maximum analyzable number of times in each reagent bottle and the number of times in pipetting. When the result of the calculation reaches zero, the effective quantity of the reagent solution is regarded as exhausted and the operation of distributive injection from the reagent bottle is stopped (step 49). At the same time, the reagent bottle is regarded as used and the code (number) peculiar to the reagent bottle is registered into the used-bottle-code memory area. Further, an alarm for requesting the reagent bottle to be exchanged to a new one is generated in the display of the CRT 18 or in the warning indication portion 28 (step 51).

If there is no problem in the aforementioned checking steps for reagent management, the situation of the routine goes from the step 48 to the step 45 so that the reagent distributively injecting operation with respect to each reagent bottle is continued. These checking steps are executed individually with respect to a large number of reagent bottles.

As described above, according to the present invention, the respective conditions of distributive injection of reagents can be managed by reagent solution bottle. Because a degraded reagent can be prevented from being used in measurement for a corresponding analytical item, a reliable result of analysis can be obtained.

What is claimed is:

1. A reagent management method in which a reagent solution corresponding to an analytical item is delivered from any of a plurality of reagent solution bottles used for analysis of a plurality of analytical items into a reaction cell, and in which conditions of use of the respective reagent solutions are monitored, comprising the steps of:

(a) registering degraded-solution bottle identification information in a register means, said degraded-solution bottle identification information being borne by and unique to each degraded-solution reagent solution bottle, wherein a degraded-solution reagent solution bottle is a reagent solution bottle containing an unacceptably-degraded reagent solution, and from which reagent solution has been previously removed through reagent delivery by a reagent solution delivering means, (b) reading newly-set bottle identification information from a newly-set reagent solution bottle, said newly-set reagent solution bottle having been set newly in a reagent solution setting position, said newly-set bottle identification information being borne by and unique to each newly set reagent solution bottle, said reading step being performed by a reader, and (c) outputting a signal representing that the newly-set reagent solution bottle contains degraded reagent solution when the newly-set bottle identification information thereof coincides with registered degraded-solution bottle identification information.

2. A reagent management method according to claim 1, wherein reagent solution delivery by the reagent solution delivering means is disabled for any reagent solution bottle bearing bottle identification information that is registered as a degraded-solution reagent solution bottle.

3. A reagent management method according to claim 1, further comprising the step of:

delivering a degraded reagent solution from a degraded-solution reagent solution bottle into a reaction cell by said reagent solution delivering means, measuring a reaction solution obtained in the reaction cell by mixing a sample therein with the degraded reagent solution, and outputting a result of measurement obtained in said measuring step with warning information.

4. A reagent management method according to claim 1, wherein information concerning a term of validation is given to each reagent solution bottle in advance so that when a reagent solution bottle is set in the reagent setting position, a judgment is made as to whether the term of validation of the reagent solution bottle has expired, and a warning is outputted when the judgment proves that the term of validation of the reagent solution bottle has expired.

5. A reagent management apparatus having a reagent solution setting portion in which a plurality of reagent solution bottles are set in correspondence to a plurality of analytical items, delivering means for delivering a reagent solution corresponding to an analytical item into a reaction cell, and monitoring means for monitoring respective conditions of use of reagent solutions, the reagent management apparatus further comprising:

(a) a plurality of reagent solution bottles each bearing bottle identification information unique thereto, for identifying each of the reagent solution bottles, (b) storage means having a degraded-solution reagent solution bottle storage area for storing degraded-solution bottle identification information borne by and unique to each degraded-solution reagent solution bottle, wherein a degraded-solution reagent solution bottle is a reagent solution bottle containing an unacceptably-degraded reagent solution, and from which reagent solution has been previously removed through reagent delivery by the delivering means, (c) reader means for reading newly-set bottle identification information borne by and unique to each newly-set reagent solution bottle set at the reagent solution setting portion, (d) judgment means for judging whether or not the read newly-set bottle identification information coincides with stored degraded-solution bottle identification information, and (e) signal generating means for generating a signal representing that the newly-set reagent solution bottle contains a degraded reagent solution when the read newly-set bottle identification information coincides with stored degraded-solution bottle identification information.

6. A reagent management apparatus according to claim 5, wherein the monitoring means monitors a state of quantity decrease of a reagent in each reagent solution bottle in the reagent delivery, so that when a quantity of a solution in a specific reagent solution bottle is increased to be larger than that in the previous cycle of reagent delivery, the bottle identification information of the specific reagent solution bottle is registered into said storage portion.

7. A reagent management apparatus according to claim 5, wherein information concerning a term of validation is given to each reagent solution bottle in advance, and wherein reagent delivery is disabled for any reagent solution bottle which is proved to have an expired term of validation.

8. A reagent management apparatus according to claim 5, wherein the newly-set reagent solution bottle bears information of a term of validation for the reagent solution contained therein, wherein the reader means reads the information of the term of validation, wherein the judgment means judges whether the term of validation has expired, and wherein the signal generating means generates a warning in response to a determination that the term of validation has expired.

* * * * *